US005695945A

United States Patent [19]
Tsuji

[11] Patent Number: 5,695,945
[45] Date of Patent: Dec. 9, 1997

[54] METHOD OF DETECTING DAF MOLECULES IN FECES

[75] Inventor: Takao Tsuji, Okayama, Japan

[73] Assignee: Sanko Junyaku Co., Ltd., Tokyo, Japan

[21] Appl. No.: 457,778

[22] Filed: Jun. 1, 1995

[30] Foreign Application Priority Data

Jun. 1, 1994 [JP] Japan .................................. 6-142561

[51] Int. Cl.$^6$ .......................... G01N 33/574; G01N 33/53
[52] U.S. Cl. .......................... 435/7.23; 435/7.9; 435/7.92; 436/518; 436/64; 436/813
[58] Field of Search .................................. 435/7.9, 7.92, 435/7.23; 436/518, 64, 813

[56] References Cited

FOREIGN PATENT DOCUMENTS 6-317588  6/1994  Japan .
WO86/07062  12/1986  WIPO .

OTHER PUBLICATIONS

Takami et al., "Evidence for Carboxyl–Terminal Processing and Glycolipid–Anchoring of Human Carcinoembryonic Antigen", The Journal of Biological Chemistry, vol. 263, No. 25, pp. 12716–12720, Sep. 5, 1988.

Lublin et al., "Decay–Accelerating Factor: Biochemistry, Molecular Biology, and Function", Ann. Rev. Immunol., pp. 35–58, 1989.

Ropers et al., "Report of the Second International Workshop on Human Chromosome 19 Mapping", Cytogenet Cell Genet, vol.60, pp. 87–95, 1992.

Inoue et al., "Distribution of Complement Regulatory Proteins, Decay–Accelerating Factor, CD59/Homologous Restriction Factor 20 and Membrane Cofactor Protein in Human Colorectal Adenoma and Cancer", Acta Med Okayama, vol. 48, No. 5, pp. 271–277, 1994.

Mizuno et al., "Detection of Decay–Accelerating Factor in Stool Specimens of Patients with Colorectal Cancer", Gastroenterology, vol. 109, No. 3, pp. 826–831, Sep. 1995.

"Biochemical and Genetic Screening of Colorectal Cancer", Gastroenterology, vol. 109, No. 3, pp. 1003–1005, Sep. 1995.

Koretz, S., et al., Br. J. Cancer, vol. 66, 810–814, 1992.

Sugano, K., et al., Jpn. J. Cancer Res., vol. 80, 1156–1160, Dec. 1989.

Hara et al., Chemical Abstracts, vol. 120, No. 15, Apr. 11, 1994, Columbus, Ohio USA, Abstract No. 189246v p. 807.

Davitz et al., Chemical Abstracts, vol. 106, No. 23, Jun. 8, 1987, Columbus, Ohio USA, Abstract No. 194206x, p. 552.

*Primary Examiner*—Toni R. Scheiner
*Attorney, Agent, or Firm*—Wenderoth, Lind & Ponack

[57] ABSTRACT

A method of easily detecting the occurrence of colorectal cancer in the absence of occult blood is provided by measuring decay accelerating factor (DAF) molecules which are synthesized by colorectal cancer cells and present in feces. The method includes reacting an anti-DAF antibody with a supernatant of a fecal solution and measuring an amount of the antibody which has bonded to DAF molecules by an antigen-antibody reaction with the DAF molecules in the supernatant.

26 Claims, 2 Drawing Sheets

METHOD OF DETECTING DAF MOLECULES IN FECES

BACKGROUND OF THE INVENTION

1. Field of the Invention

The present invention relates to a method of detecting decay accelerating factor (DAF) molecules in feces. More specifically, it relates to a method of detecting DAF molecules in feces, useful for detecting colorectal cancer by examining the concentration of DAF molecules in feces.

2. Description of Related Art

In a general medical examination, it is conventional practice to detect occult blood in feces for detecting colorectal cancer. When occult blood is detected in feces, the photographic examination based a contrast medium used in the large intestine and the colorectal endoscopic examination of the colon are carried out to detect colorectal cancer. However, occult blood is not always found in feces from the colorectal cancer patients. For this reason, when the examination is based on the detection of occult blood in feces alone, colorectal cancer is sometimes not detected.

It has been recently immunologically found that the expression of DAF molecules is enhanced in a colorectal cancer tissue. DAF molecules, i.e., decay accelerating factor, are glycoproteins which regulate the activation of the autologous complement cascade by promoting the catabolism of C3 and C5 convertases. It has been revealed that almost no DAF molecules are expressed in a normal epithelial cell on colorectal mucosa, but that DAF molecules are intensely expressed, particularly, on an apical surface of a cancer gland duct of a colorectal cancer cell.

The present inventors have assumed that feces from colorectal cancer patients show an increased amount of DAF molecules.

SUMMARY OF THE INVENTION

It is an object of the present invention to provide a method of easily detecting the occurrence of colorectal cancer.

It is another object of the present invention to provide a method of detecting colorectal cancer by measuring DAF molecules which are synthesized by colorectal cancer cells and present in feces.

It is further another object of the present invention to provide a method of detecting colorectal cancer in the absence of occult blood, by measuring DAF molecules which are synthesized by colorectal cancer cells and present in feces.

According to the present invention, there is provided a method of detecting DAF molecules in feces, which comprises reacting an anti-DAF antibody with a supernatant of a fecal solution and measuring an amount of the antibody which has bonded to DAF molecules by an antigen-antibody reaction with the DAF molecules in the supernatant.

DETAILED DESCRIPTION OF THE INVENTION

Figure 1:
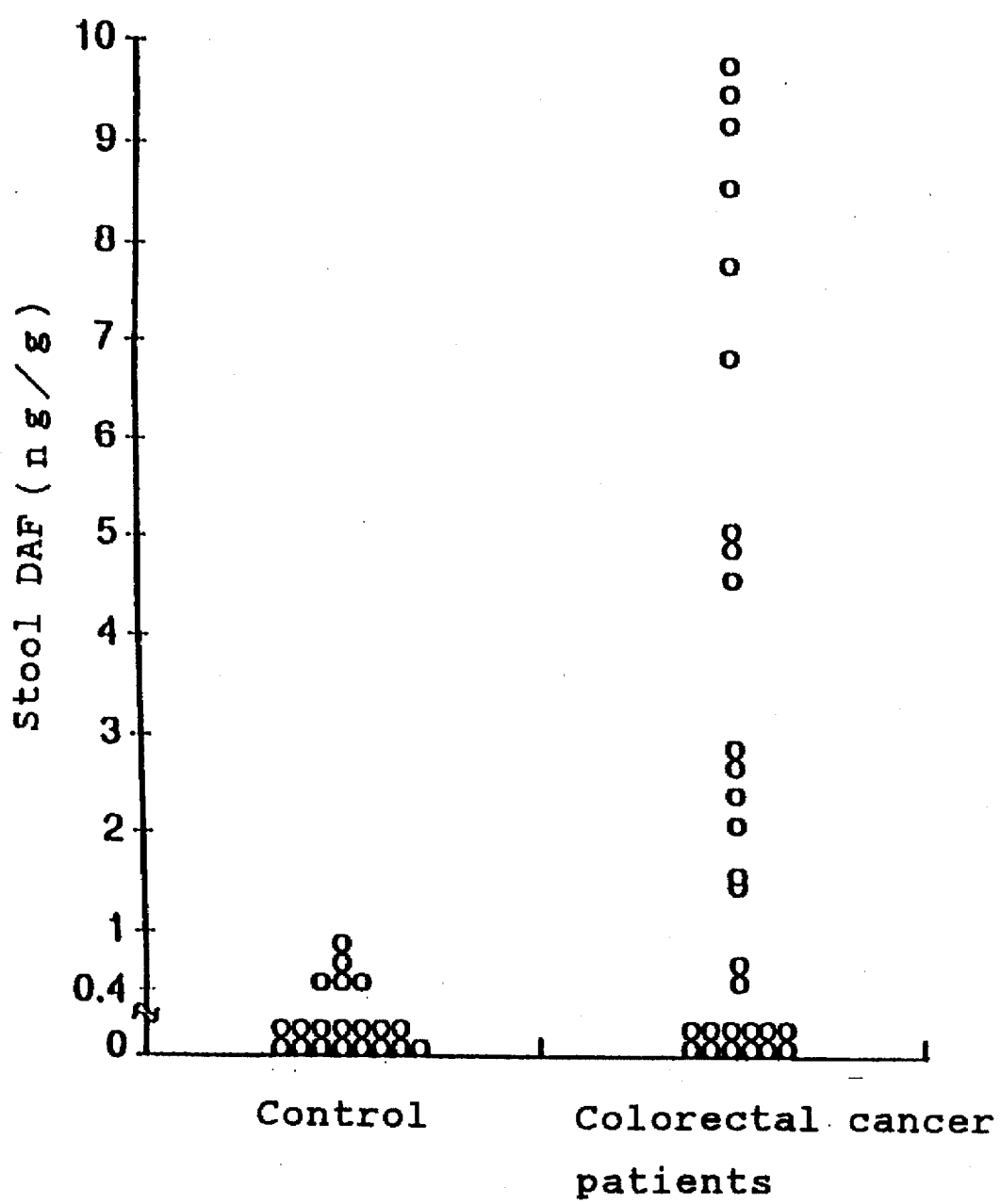
FIG. 1 is a graph showing DAF concentrations in feces from colorectal cancer patients and a control group of patients having no colorectal cancer.

The detection method of the present invention will be explained in detail hereinafter.

Preparation of supernatant of fecal solution

A predetermined amount of feces are mixed with a buffer solution, the mixture is stirred, and then a supernatant is separated by centrifugation.

Preparation of anti-DAF antibody

Human DAF molecules are purified from erythrocyte membrane to prepare anti-DAF monoclonal antibody and anti-DAF polyclonal antibody.

Measurement of DAF molecules in feces

1) The anti-DAF monoclonal antibody or the anti-DAF polyclonal antibody is converted to a solid phase on a microtiter plate or beads and reacted with the supernatant of feces.

2) After the above reaction product is washed, an enzyme- or radioactive substance-labeled anti-DAF monoclonal antibody or anti-DAF polyclonal antibody is reacted with the washed reaction product to measure an amount of the bonded DAF molecules.

Alternatively,

2') After the above reaction product is washed, an anti-DAF monoclonal antibody or an anti-DAF polyclonal antibody is reacted with the reaction product. The resultant reaction product is washed, and then reacted with an enzyme- or radioactive substance-labeled antimonoclonal immunoglobulin antibody or antipolyclonal immunoglobulin antibody to measure the bonded second anti-DAF antibodies.

Preparation of calibration curve

A calibration curve is prepared on the basis of purified DAF in a known amount, and the DAF amount in a sample is calculated on the basis of the calibration curve and expressed as an amount in 1 g of feces.

According to the method of the present invention, an amount of at least 0.4 ng in 1 g of feces can be accurately measured.

DAF in feces from a colorectal cancer patient, detected by the method of the present invention, is assumed to be derived from cancer cells or erythrocyte in blood from colorectal cancer. Since, however, DAF is detected even in feces from a colorectal cancer patient who is negative with regard to occult blood, it is assumed that above detected DAF includes DAF in feces, derived from cancer cells. DAF in feces from a group of patients having no colorectal diseases (to be referred to as "control group" hereinafter) is less than the detectable sensitivity, and it is therefore assumed that normal colorectal mucosa secretes no DAF.

Colorectal cancer screening based on occult blood in feces has a problem of false negative results because colorectal cancer does not cause detectable bleeding in some cases. The method of the present invention is advantageous in that colorectal cancer which causes no detectable bleeding can be sometimes detected by detecting DAF in feces.

The present invention will be explained more in detail hereinafter with reference to Examples, in which "%" stands for "% by weight" unless otherwise specified.

EXAMPLE AND COMPARATIVE EXAMPLE

Preparation of supernatant of fecal solution

Feces in an amount of 1 to 5 g were mixed with a buffer solution in the same amount as that of the feces, and the mixture was stirred. The buffer solution was a sodium phosphate buffer solution containing 1% of bovine serum albumin, 0.05% of Tween and 1 mM of phenylmethylsulfonyl fluoride. The stirred mixture was centrifugally separated for 15 minutes at 20,000 g. The supernatant was sampled and freeze-stored at −80° C. before the measurement.

preparation of anti-DAF mouse monoclonal antibody

1) Purification of human DAF molecules

Erythrocyte was separated from 50 ml of human blood, and 400 ml of a 5 mM sodium phosphate buffer solution containing 1 mM of EDTA and 0.1 mM of phenylmethylsulfonyl fluoride was added to the separated erythrocyte. The mixture was stirred and centrifugally separated at 48,000 g, and a precipitate of an erythrocyte substrate was collected.

The above erythrocyte substrate in an amount of 1 g was diluted to 5 mg/ml with a 5 mM sodium phosphate buffer solution, and 80 ml of butanol was added. The mixture was stirred and then centrifugally separated at 12,000 g, and an aqueous layer between an upper layer of butanol and a lower layer of a precipitate was recovered. Then, the aqueous layer was subjected to a DEAE-Sephacel ion exchange column, and a crude fraction of DAF molecules was separated with a 0.02 M tris buffer solution containing 0.04 M of sodium hydrochloride and 0.1% of Nonidet P-40 (NP-40).

Further, the crude fraction of DAF was subjected to a phenyl-Sepharose column, and the DAF was separated with a 0.04 M sodium phosphate buffer solution containing 0.3 M of sodium hydrochloride and 0.1% of P-40 and then with a 0.05 M sodium phosphate buffer solution containing 0.05 M of sodium hydrochloride and 1% of NP-40. Further, the DAF was separated through a hydroxyapatite column.

2) Preparation of anti-DAF mouse monoclonal antibody

A BALB/C mouse was immunized with a suspension of 5 µg of the purified DAF in a Freund adjuvant containing dead tuberculosis bacillus twice at an interval of one week. After three weeks, spleen cells were taken out and fused with NS-1 mouse myeloma cells using polyethylene glycol. The supernatant of a culture of the so-prepared hybridoma was reacted with a nitrocellulose membrane blotted with the purified DAF, and screened by detecting bonded mouse monoclonal antibody with an ABC kit supplied by Vector Laboratories, to give hybridomas which produced four kinds of anti-DAF monoclonal antibodies.

All of the produced monoclonal antibodies were IgG1 kappa. Of these four kinds of monoclonal antibodies, 1C6 monoclonal antibody which recognized an active portion of DAF molecules was used for the detection of stool DAF. Hybridoma which produced 1C6 monoclonal antibody was intraperitoneally injected into a mouse to prepare ascites, which was sampled.

1C6 anti-DAF monoclonal antibody IgG was separated and purified from the ascites by an ammonium sulfate precipitation method and DEAE chromatography (using "Toyopearl" supplied by Tosoh Corp.).

Preparation of rabbit anti-DAF polyclonal antibody

The purified DAF was infused into 10 ml of rabbit erythrocyte by incubating it at 37° C. for 1 hour. This erythrocyte was washed and dissolved, and cytoplasmic membrane was centrifugally separated. The cytoplasmic membrane was suspended in a Freund adjuvant containing dead tuberculosis bacillus, and the rabbit from which the erythrocyte had been separated was immunized with the so-prepared suspension. Blood was taken from the immunized rabbit, serum was separated, and rabbit IgG was separated and purified by an ammonium sulfate precipitation method and DEAE chromatography.

The specificity of the above-obtained antibody was examined by an immunoblotting method. That is, a crude extract of human erythrocyte substrate was electrophoresed in SDS polyacrylamide gel, blotted into a nitrocellulose membrane, and reacted with the rabbit DAF polyclonal antibody. When bonded rabbit IgG antibody was detected with a Vectastain ABC kit (Vector Laboratories, Inc., CA), a single band was detected in a site corresponding to the molecular weight of 70 kD of the DAF molecules, so that the specificity of the rabbit anti-polyclonal antibody was confirmed.

Measurement of DAF molecules in feces

The 1C6 DAF mouse monoclonal antibody having a concentration of 2 µg/ml was placed in wells of a microtiter plate in an amount of 100 µl per well. After a reaction at 4° C. for 12 hours, a sodium phosphate buffer solution containing 1% of bovine serum albumin was added, and the mixtures were allowed to stand at 4° C. overnight. After the monoclonal antibody was washed, the supernatant of the fecal solution was added in an amount of 100 µl per well, and incubated at 4° C. overnight. After washing, the rabbit DAF polyclonal antibody IgG having a concentration of 4 µg/ml was added in an amount of 100 µl per well, and after the mixtures were allowed to react at room temperature for 2 hours, the wells were washed. Then, a peroxidase-labeled goat F(ab)'2 anti-rabbit IgG (supplied by TAGO, U.S.A) was added in an amount of 100 µl per well, and after the mixtures were allowed to react at room temperature for 2 hours, the reaction products were washed and color-developed with 2,2'-azino-di-3-ethylbenzothiazoline-6-sulfonic acid. The resultant reaction products were measured for absorbance at 415 nm with an automatic ELISA plate reader.

Preparation of calibration curve

The purified DAF in an amount of 0.1 ng to 10 ng per well was added and allowed to react to prepare a calibration curve. The amount of DAF in samples were calculated on the basis of the calibration curve and expressed as an amount in 1 g of feces.

Method of detecting occult blood in feces

Guaiac method: Examined with a fecal occult blood slide supplied by Shionogi & Co., Ltd.

Immunological method: Examined with an OC-Hemodia-Eiken supplied by Eiken Chemical Co., Ltd., Japan.

Figure 2:
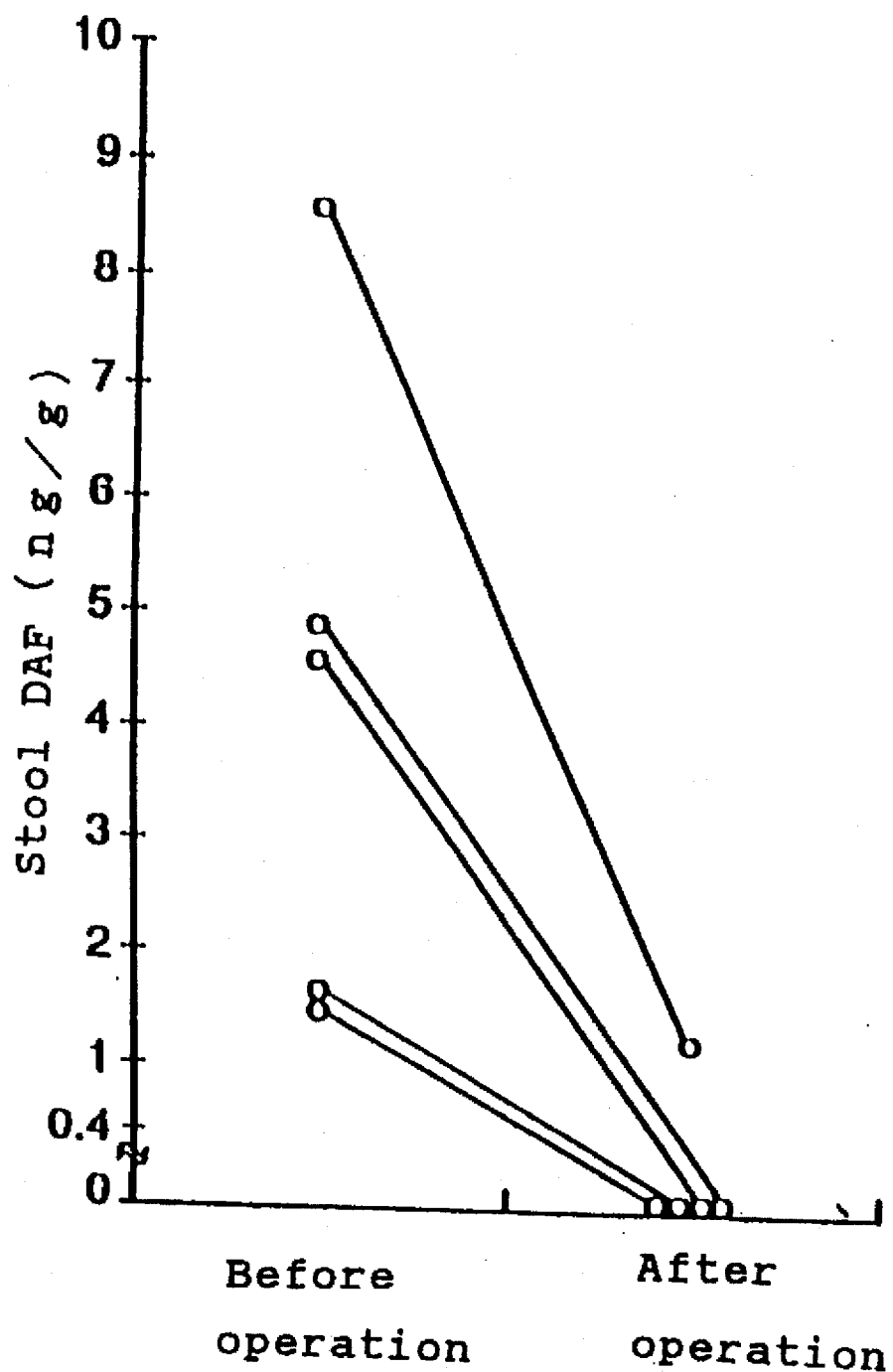
FIG. 2 is a graph showing changes of DAF concentrations in feces from pre-operation of colorectal cancer to post-operation.

The method of detecting DAF molecules in feces, provided by the present invention, was studied for its usefulness on the basis of the above Method of measuring DAF in feces and the above Method of detecting occult blood in feces with regard to 29 patients having colorectal cancer and Control group of 20 people having no colorectal cancer. FIGS. 1 and 2 and Tables 1 to 4 show the results.

FIG. 1 shows concentrations of DAF molecules in feces from 29 patients having colorectal cancer and Control group of 20 people having no colorectal cancer. In Control group, the concentrations of DAF molecules in feces from 15 people were below the detectable amount, and the concentrations of DAF molecules in feces from 5 people were 1 ng in 1 g of feces, or less. On the other hand, in the 29 patients having colorectal cancer, the concentrations of DAF molecules in feces from 15 patients were 1 ng in 1 g of feces, or more, the concentrations in feces from 2 patients were 0.4 to 1 ng, and these concentrations in feces from 12 patients were below the detectable amount. It is seen that the concentrations of DAF molecules in feces from colorectal cancer patients and those in feces from Control group have a significant difference ($p=0.006$). Further, when the 1 ng/g of DAF molecules in feces is taken as a boundary, a group of colorectal cancer patients and Control group can be discriminated. When patients showing a concentration of at least 1 ng/g of DAF molecules in feces are taken as positive, the positive ratio of colorectal cancer patients was 52% (15 patients/29 patients), or showed a significant difference over 0% of Control group (p=0.0001).

FIG. 2 shows differences between concentrations of DAF molecules in feces before operation of colorectal cancer and concentrations of DAF molecules in feces after the operation of the colorectal cancer with regard to 5 colorectal cancer patients who preoperatively showed the elevated level of DAF molecules in feces. The concentrations of DAF molecules in feces from four patients out of the five patents decreased to be below the detectable sensitivity, and that in feces from one patient decreased from 8.6 ng/g to 1.4 ng/g.

Table 1 shows the result of studies of the correlation between the ratio of detection of DAF molecules in feces and the size of colorectal cancer.

TABLE 1

|       | ≦2 cm* | 2–5 cm | >5 cm |
|-------|--------|--------|-------|
| DAF + | 3      | 7      | 5     |
| −     | 2      | 10     | 2     |
| Total | 5      | 17     | 7     |

Notes:
+ shows that the concentration of DAF molecules was at least 1 ng/g
− shows that the concentration of DAF molecules was lower than 1 ng/g.
*size of tumor DAF molecules were detected in feces without having anything to do with colorectal cancer sizes.

Table 2 shows the result of studies of the correlation between the ratio of detection of DAF molecules in feces and colorectal cancer sites.

TABLE 2

|       | Rectum | Rectosigmoid and descending colon | Ascending colon and cecum |
|-------|--------|-----------------------------------|---------------------------|
| DAF + | 4      | 7                                 | 4                         |
| −     | 3      | 7                                 | 4                         |
| Total | 7      | 14                                | 8                         |

Notes:
+ and − have the same meanings as those in notes to Table 1.

DAF molecules were detected in feces without having anything to do with colorectal cancer sites.

Table 3 shows the result of studies of the correlation between the ratio of detection of DAF molecules in feces and the TNM stage.

TABLE 3

|       | I* | II | III | IV |
|-------|----|----|-----|----|
| DAF + | 3  | 6  | 4   | 2  |
| −     | 1  | 6  | 5   | 2  |
| Total | 4  | 12 | 9   | 4  |

Notes:
+ and − have the same meanings as those in notes to Table 1.
*TNM stage of colorectal cancer DAF molecules were detected in feces without having anything to do with TNM stage of colorectal cancer.

Table 4 shows the result of studies of the correlation between the ratio of detection of DAF molecules in feces and fecal occult blood testing.

TABLE 4

|                  | DAF + | DAF − | Total |
|------------------|-------|-------|-------|
| Guaiac test +    | 10    | 6     | 16    |
| −                | 5     | 8     | 13    |
| Immunological +  | 11    | 12    | 23    |
| test −           | 4     | 2     | 6     |

In 29 patients having colorectal cancer, 16 patients (55%) were positive in the method of detection of occult blood in feces according to Guaiac method, and 23 patients (79%) were positive in the method of detection of occult blood in feces according to the immunological method. Further, DAF molecules in feces were detected in 5 patients out of 13 patients for whom the detection according to Guaiac method was negative and in 4 patients out of 6 patients for whom the detection according to the immunological method was negative. In Control group, two people showed that the fecal occult blood testing was positive while the detection of DAF molecules in feces was negative.

According to the method of detecting DAF molecules in feces, provided by the present invention, there is provided a method which enables the detection of DAF in feces from colorectal cancer patients, which shows a significant difference over the detection of DAF in feces from Control group of people having no colorectal cancer. Further, according to the method of the present invention, there is provided a method which enables the detection of DAF in feces from colorectal cancer patients for whom the detection of occult blood in feces is negative.

What is claimed is:

1. A method for detecting decay accelerating factor (DAF) molecules in feces, which comprises:

reacting a first antibody which specifically binds to a DAF molecule with a supernatant of a fecal solution to form a first complex of the first antibody with a DAF molecule present in the supernatant of the fecal solution, and measuring the amount of first complexes formed to detect the amount of DAF molecules in the supernatant of the fecal solution.

2. The method according to claim 1, wherein the first antibody is a monoclonal antibody.

3. The method according to claim 1, wherein the first antibody is a polyclonal antibody.

4. The method according to claim 1, wherein the first antibody is immobilized on a solid phase before reacting with the supernatant of the fecal solution.

5. The method according to claim 1, wherein the amount of first complexes measured by an enzyme immunoassay or radioimmunoassay.

6. The method according to claim 1, wherein the amount of first complexes is measured by reacting the first complexes with a second antibody which specifically binds to the DAF molecule at a different epitope than the first antibody to form a second complex of the first antibody, DAF molecule and second antibody, and measuring the amount of second complexes to detect the amount of DAF molecules in the supernatant of the fecal solution.

7. The method according to claim 6, wherein the second antibody is labeled with an enzyme.

8. The method according to claim 6, wherein the second antibody is labeled with a radioactive substance.

9. The method according to claim 6, wherein the amount of second complexes is measured by reacting the second antibody with a third antibody which specifically binds to the second antibody.

10. The method according to claim 9, wherein the third antibody is labeled with an enzyme.

11. The method according to claim 9, wherein the third antibody is labeled with a radioactive substance.

12. The method according to claim 6, wherein the first antibody is a monoclonal antibody and the second antibody is a polyclonal antibody.

13. The method according to claim 6, wherein the first antibody and second antibody are both monoclonal antibodies.

14. A method for detecting colorectal carcinoma, which comprises:

reacting a first antibody which specifically binds to a DAF molecule with a supernatant of a fecal solution to form a first complex of the first antibody with a DAF molecule present in the supernatant of the fecal solution, and measuring the amount of first complexes formed to detect the amount of DAF molecules in the supernatant of the fecal solution, to thereby detect colorectal carcinoma.

15. The method according to claim 14, wherein the first antibody is a monoclonal antibody.

16. The method according to claim 14, wherein the first antibody is a polyclonal antibody.

17. The method according to claim 14, wherein the first antibody is immobilized on a solid phase before reacting with the supernatant of the fecal solution.

18. The method according to claim 14, wherein the amount of first complexes is measured by an enzyme immunoassay or radioimmunoassay.

19. The method according to claim 14, wherein the amount of first complexes is measured by reacting the first complexes with a second antibody which specifically binds to the DAF molecule at a different epitope than the first antibody to form a second complex of the first antibody, DAF molecule and second antibody, and measuring the amount of second complexes to detect the amount of DAF molecules in the supernatant of the fecal solution.

20. The method according to claim 19, wherein the second antibody is labeled with an enzyme.

21. The method according to claim 19, wherein the second antibody is labeled with a radioactive substance.

22. The method according to claim 19, wherein the amount of second complexes is measured by reacting the second antibody with a third antibody which specifically binds to the second antibody.

23. The method according to claim 22, wherein the third antibody is labeled with an enzyme.

24. The method according to claim 22, wherein the third antibody is labeled with a radioactive substance.

25. The method according to claim 19, wherein the first antibody is a monoclonal antibody and the second antibody is a polyclonal antibody.

26. The method according to claim 19, wherein the first antibody and second antibody are both monoclonal antibodies.

* * * * *

UNITED STATES PATENT AND TRADEMARK OFFICE
CERTIFICATE OF CORRECTION

PATENT NO. : 5,695,945
DATED : December 9, 1997
INVENTOR(S) : TAKAO TUSJI and MOTOWO MIZUNO It is certified that error appears in the above-identified patent and that said Letters Patent is hereby corrected as shown below:

On the title page, Item [75], before "Okayama", insert the following --Motowo Mizuno, both of --.

Signed and Sealed this

Sixth Day of October, 1998

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,695,945

DATED : December 9, 1997

INVENTOR(S) : Takao TSUJI and Motowo MIZUNO

It is certified that error appears in the above-identified patent and that said Letters Patent is hereby corrected as shown below:

On the title page, Item [75], before "Okayama", insert the following --Motowo Mizuno, both of--.

This certificate supersedes Certificate of Correction issued October 6, 1998.

Signed and Sealed this

Twenty-fifth Day of April, 2000

*Attest:*

Q. TODD DICKINSON

*Attesting Officer*  *Director of Patents and Trademarks*